United States Patent [19]

Archibald et al.

[11] 4,235,915
[45] Nov. 25, 1980

[54] β ADRENERGIC BLOCKING PIPERIDINO UREAS AND THIOUREAS

[75] Inventors: John L. Archibald, Windsor; Terence J. Ward, Slough, both of England

[73] Assignee: John Wyeth & Brother Limited, Taplow, England

[21] Appl. No.: 857,334

[22] Filed: Dec. 5, 1977

[30] Foreign Application Priority Data

Dec. 11, 1976 [GB] United Kingdom ............... 51781/76

[51] Int. Cl.³ ............................................ A61K 31/445
[52] U.S. Cl. .................. 424/267; 260/340.6; 546/197; 546/224
[58] Field of Search ................... 260/293.58; 424/267; 546/197

[56] References Cited

U.S. PATENT DOCUMENTS

| | | | |
|---|---|---|---|
| 3,910,930 | 10/1975 | Janssen et al. | 260/293.58 |
| 3,919,242 | 11/1975 | Cavalla et al. | 260/293.58 |
| 4,061,641 | 12/1977 | Archibald et al. | 260/293.61 |

FOREIGN PATENT DOCUMENTS 1345872 2/1974 United Kingdom.
1404003 8/1975 United Kingdom ................ 260/293.61

OTHER PUBLICATIONS

Wellens, D., et al., *Arch. Int. Pharmacodyn.*, 215, 91–103 (1975) and 215, 119–132 (1975).
Van Zwieten, P., *Arch. Int. Pharmacodyn.*, 215, 104–118 (1975).

*Primary Examiner*—Henry R. Jiles
*Assistant Examiner*—Richard A. Schwartz
*Attorney, Agent, or Firm*—Arthur E. Wilfond

[57] ABSTRACT

Compounds of formula

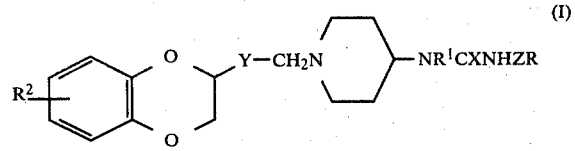

in which
X represents oxygen or sulphur;
Y represents —CHOH— or

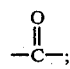

Z represents

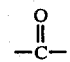

or a direct bond;
R represents cycloalkyl group having 5 to 7 carbon atoms or an optionally substituted aryl or heteroaryl radical, or when —Z— is a direct bond R also represents hydrogen;
$R^1$ represents hydrogen or lower alkyl.
and
$R^2$ represents hydrogen, halogen, lower alkyl or lower alkoxy;
or
a pharmaceutically acceptable acid addition or quaternary ammonium salt thereof, are disclosed which reduce heart rate or have hyperglycaemic activity.

1 Claim, No Drawings

β ADRENERGIC BLOCKING PIPERIDINO UREAS AND THIOUREAS

This invention relates to piperidine derivatives having pharmaceutical activity, to processes for their preparation, to pharmaceutical compositions containing them, and to intermediates useful in their preparation.

U.S. Pat. No. 3,910,930 issued Oct. 7th, 1975 describes 1-{1-[2-(1,4-benzodioxan-2-yl)-2-hydroxyethyl]-4-piperidyl}-2-benzamidazolinones useful as antihypertensive agents. One of the compounds disclosed therein, namely erythro-1-{1-[2-(1,4-benzodioxan-2-yl)-2-hydroxyethyl]-4-piperidyl}-2-benzimidazolinone, has been further evaluated and its mode of action discussed in Arch, int Pharmacodyn. 215, 91–132 (1975). Heart rate is reduced although only significantly at high doses. No α- or β- adrenoceptor blocking activity has been reported for this compound.

1-(Benzodioxan-2-yl alkyl)-4-benzamido-piperidine derivatives are disclosed in U.S. Pat. No. 3,919,242 issued Nov. 11th, 1975 which are useful in the treatment of disorders and diseases of the cardiovascular system. No α- or β- blocking activity has been reported for these compounds.

This invention provides compounds having the formula

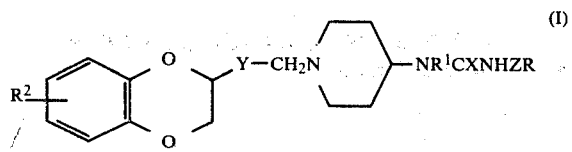

wherein X represents oxygen or sulphur; Y represents —CHOH— or

Z represents

or a direct bond; R represents cycloalkyl having 5 to 7 carbon atoms or an optionally substituted aryl, or heteroaryl radical, or when Z is a direct bond R can also represent hydrogen; $R^1$ represents hydrogen or lower alkyl; $R^2$ represents hydrogen, halogen, lower alkyl or lower alkoxy, and acid addition and quaternary ammonium salts thereof.

The term "lower" as used herein in connection with a group or molecule means that the group or molecule contains 1 to 6 carbon atoms.

Examples of $R^2$ are hydrogen, methyl, ethyl, propyl, chlorine, bromine, methoxy, ethoxy and propoxy.

Examples of R when other than hydrogen are: aryl radicals such as phenyl and phenyl substituted by one or more groups such as lower alkyl (e.g. methyl, ethyl, propyl or isopropyl), lower alkoxy (e.g. methoxy, ethoxy, propoxy or isopropoxy), methylenedioxy, halogen (e.g. fluorine, chlorine or bromine) perhalolower alkyl such as trifluoromethyl, nitro, amino and hydroxy; cycloalkyl radicals such as cyclohexyl and heteroaryl radicals, wherein the heteroatom is selected from oxygen, nitrogen or sulphur such as thienyl (e.g. 2-thienyl) furyl (e.g. 2-furyl) and pyridyl (e.g. 3-pyridyl).

Examples of $R^1$ are hydrogen methyl, ethyl, n-propyl.

Examples of acid addition salts are those formed with pharmaceutically acceptable acids such as the hydrochloride, sulphate, phosphate, acetate, maleate, fumarate, tartrate, formate, methanesulphonate, p-toluensulphonate, benzoate, succinate, lactate and salicylate.

Examples of quaternary ammonium compounds are those formed with alkyl and aralkyl halides, particularly methyl and ethyl halides such as ethyl bromide and methyl iodide, and benzyl halides such as benzyl chloride.

It will be apparent to those skilled in the art that the compounds of formula I possess at least one, and sometimes two asymmetric centres and hence optical isomers and sometimes diastereoisomers are possible. All such optically active forms and mixtures thereof, are intended to be included within the scope of this invention. More particularly when Y represents the group —CHOH— in formula I above then two asymmetric centres are present and therefore such a compound can exist in one of four optically active forms, i.e. two pairs of enantiomers—one pair of enantiomers being the diastereoisomers of the other pair. Such diastereoisomeric forms are termed threo and erythro and have the relative configurations shown below;

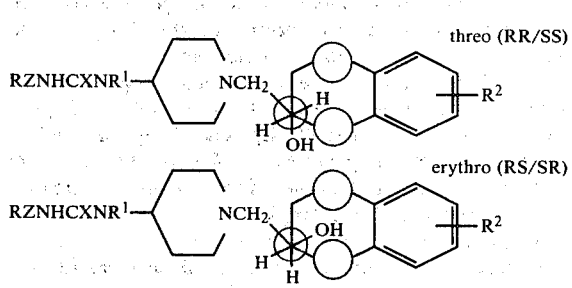

Separation of diastereoisomers and enantiomers may be effected by standard techniques known in the art.

Compounds of formula I, wherein Y is CHOH, having the erythro configuration are particularly preferred.

The compounds of this invention possess pharmaceutical activity and some are intermediates for other compounds of this invention.

More particularly when Y is —CHOH— the compounds of formula I possess the ability to reduce heart rate when administered in a standard test to renal hypertensive rats. The erythro series of diastereoisomers are particularly active in reducing heart rate. Representative of the compounds of formula I wherein Y is —CHOH— is erythro 1-benzoyl-3-[1-(2--[1,4-benzodioxan-2-yl]-2-hydroxyethyl)-piperid-4-yl]urea, hydrochloride, which possesses marked ability to reduce heart rate in the above mentioned test, producing a 48.5% and 51.5% decrease in heart rate at a time period of 2 hours and 6 hours respectively after dosing.

The compounds of formula I wherein Y is —CHOH— also possess hypotensive activity when administered in a standard test to normotensive rats. Representative of such compounds are threo-and erythro-1-benzoyl-3-[1-(2-[1,4-benzodioxan-2-yl]-2-hydroxyethyl)piperid-4-yl]urea hydrochloride, which compounds produced a lowering in diastolic blood pressure of ≧30 mm Hg sustained for 15 minutes. For the threo isomer the dose level was 12.8 mpk (2 rats)

and for the erythro the dose level was 12.8 mpk (1 rat) and 6.4 mpk (1 rat).

The erythro series of diastereoisomers also possess α and β adrenergic blocking activity as evidenced by standard tests on isolated animal tissue. Thus the representative compound erythro-1-benzoyl-3-[1-(2-[1,4-benzodioxan-2-yl]-2-hydroxyethyl)piperid-4-yl]urea hydrochloride was found to possess an α-adrenoceptor blockade $PA_2$ value of 7.0 when tested on rat perfused mesentery. This compound showed a $PA_2$ value of 8.0 when tested for $β_1$-adrenoceptor blocking activity in guinea-pig spontaneously beating atria using concentrations showing minimal cardioinhibition. It also showed a $PA_2$ value of 6.8 when tested for $β_2$-adrenoceptor activity on guinea-pig isolated tracheal spiral.

Compounds possessing the ability to lower heart rate and/or possessing α and β adrenergic blocking activity may be useful in the treatment or prophylaxis of coronary artery disorders.

Compounds of formula I wherein Y represents —CO— possess hyperglycaemic activity, as shown by a standard test on warm blooded animals. The compounds can be tested for hyperglycaemic activity by the following procedure.

Male rats weighing 170–200 grams are fasted overnight. A control blood sample taken from the tail and the sample of test compound is then administered by stomach tube. Subsequent blood samples are taken at hourly intervals for three hours and the change in the blood sugar concentration is determined.

In this procedure it was found that a representative compound of formula (I) namely 1-benzoyl-3-[1-(2-[1,4-benzodioxan-2-yl]-2-oxoethyl)piperid-4-yl]urea, hydrochloride produced an increase in blood sugar of more than 20% for more than one of the hourly test samples when administered at 50 mpk.

Hyperglycaemic agents can be of use for administration to patients having too low a blood sugar concentration following, for example, administration of too large a dose of hypoglycaemic agent such as insulin. Hyperglycaemic agents can also be used to produce hyperglycaemic animals which can be used in screening for hypoglycaemic compounds in pharmacological procedures.

It is possible to interconvert the compounds of formula I and hence all the compounds are useful as intermediates for other compounds of formula I. Thus compounds of formula I wherein Y represents —CO— are useful for preparing compounds of formula I wherein Y represents —CHOH—. Compounds of formula I wherein RZ—represents an acyl group, especially those as herein defined, are useful in the preparation of compounds of formula I wherein R is H and Z is a direct bond; which compounds can be acylated to give other compounds of this invention wherein RZ— is an acyl group.

This invention also provides processes for preparing the compounds of formula I.

One such process for preparing a compound of formula I wherein Y represents —CO— or —CHOH— comprises reacting a compound of formula

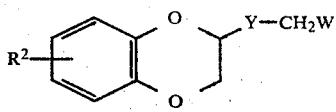

(II)

wherein $R^2$ and Y are as defined above and W represents a halogen (e.e. chlorine or bromine) or equivalent replaceable radical such as an organic sulphonyl radical, e.g. tosylate (—Otosyl), with a compound of formula

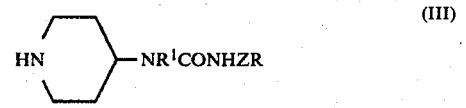

(III)

wherein Z, R and $R^1$ are as defined above; R being other than hydrogen. Such a reaction is conveniently carried out in the presence of base, e.g. an alkali metal carbonate such as potassium carbonate or a lower alkyl amine, e.g. triethylamine, in a suitable inert solvent, e.g. dimethylformamide, dichloromethane, isopropanol and the like.

A further process for preparing compounds of formula I comprises reacting a compound of formula

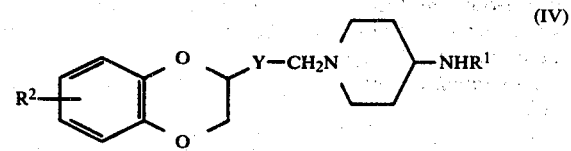

(IV)

wherein $R^1$, $R^2$ and Y are as hereinbefore defined with a compound of formula (V)

RZN=C=X    (V)

wherein X, Z and R are as defined in connection with formula I, R being other than hydrogen. This reaction should be conducted under mild conditions to avoid the possibility of reaction between the amine IV (when Y is —CO—) and the oxoethylene radical of another molecule of amine IV giving a Schiffs base. Usually the reaction to form the compound of formula I takes place at room temperature.

The starting materials of formula IV wherein $R^1$ is hydrogen may be prepared by methods described in our British Specification No. 1,345,872. The starting materials of formula (IV) wherein $R^1$ is lower alkyl may be prepared by alkylating corresponding compounds of formula IV wherein $R^1$ is hydrogen, or by methods analogous to those described in Specification No. 1,345,872.

The starting materials of formula III may be prepared by reacting 1-benzyl-4-aminopiperidine with a compound of formula V wherein X is oxygen and removing the 1-benzyl group by hydrogenolysis.

Compounds of formula I wherein R is hydrogen may be prepared by hydrolysis, e.g. using aqueous sodium hydroxide, of the corresponding compounds of formula

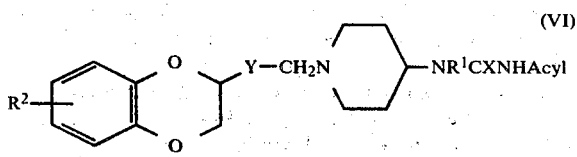

(VI)

wherein X, $R^1$, $R^2$ and Y are as defined above the Acyl represents an acyl radical, e.g. aroyl or heteroaroyl.

Once a compound of formula I wherein R is hydrogen has been prepared then that compound may be acylated to give other compounds of this invention wherein RZ— represents an acyl radical, for example, using an active derivative of an acid of formula

  (VII)

wherein R is cycloalkyl of 5 to 7 carbon atoms, aryl or heteroaryl. Examples of reactive derivatives of the acid of formula VII are the halide, e.g. the chloride, and the anhydride.

If necessary, in any of the reactions herein described, reactive substituent groups may be blocked during a reaction and released at a later stage.

A further method of preparing compounds of formula I wherein $R^1$ is a hydrogen and Z is a direct bond comprises reacting a compound of formula IX:

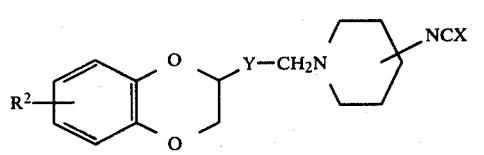

with an amine of formula

  (X)

wherein X, Y as defined above and R is as defined in connection with formula I except hydrogen. This reaction should be conducted under mild conditions to avoid any possibility of the amine reacting with the oxoethylene group to form a Schiffs base.

Compounds of formula (IX) may be prepared by treatment of a compound of formula IV, wherein $R^1$ is hydrogen with phosgene followed by treatment of the product with calcium oxide according to the following reaction scheme:

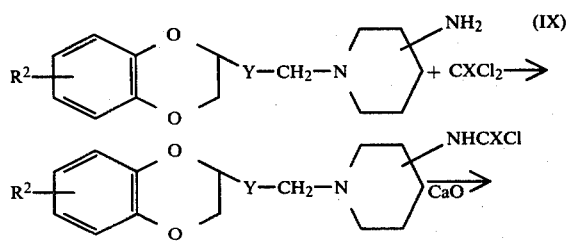

Other standard methods may be used to prepare compound (IX).

A method for preparing compounds of formula I wherein R is hydrogen and X is oxygen comprises reacting a compound of formula IV with nitrourea ($H_2NCONH.NO_2$).

The compounds of formula (I) wherein Y is —CHOH— are also obtained by reacting a compound of formula (III)

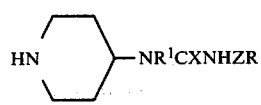  (III)

with a 2-epoxyethyl-1, 4-benzodioxan of formula X

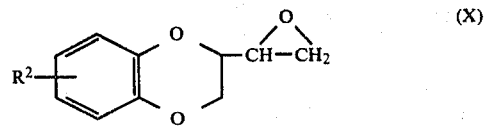  (X)

In a suitable organic solvent such as an aromatic hydrocarbon for example, benzene, toluene, xylene and the like; a halogenated hydrocarbon such as chloroform and methylene chloride; or a lower alkanol, such as, for example, methanol, ethanol, 2-propanol and the like and preferably in a mixture of an aromatic hydrocarbon and a lower alkanol. The reaction may be promoted by the addition of alkali.

Once a compound of formula I wherein Y is —CO— has been prepared then such a compound may be reduced to give other compounds of formula I wherein Y is —CHOH—. For example reduction may be effected with a hydride transfer agent such as an alkali metal borohydride, e.g. sodium borohydride, and sodium tri-t-butoxyborohydride. Other methods applicable to the reduction of a ketone to a secondary alcohol are known in the literature—see for example "Compendium of Organic Synthetic Methods" Ian T. Harrison, Shuyen Harrison, Published by Wiley Interscience, Volume I, 1971.

Once a compound of formula I wherein Y is —CHOH— has been prepared then such a compound may be oxidised to give other compounds of formula I wherein Y is —CO—. For example, chromic acid oxidation may be used to effect the above mentioned conversion. Other methods for oxidising secondary alcohols to ketones are known in the literature see, for example, the above mentioned textbook of Harrison and Harrison.

Separation of diastereoisomers and resolution of enantiomers may be effected by standard techniques known in the art after any of the above mentioned processes where racemic starting materials are employed. For example diastereoisomers can generally be separated by techniques such as fractional crystallisation or chromatography.

Alternatively it will be apparent to those skilled in the art that if it is desired to prepare a final product having a specific stereochemistry then it is possible in some instances to employ a starting material already having the desired stereochemistry. Such routes to erythro compounds of formula I are preferred. For example erythro compounds of formula (IV) as defined above may be reacted with compounds of formula V to give corresponding erythro compounds of formula I.

Erythro compounds of formula IV may be prepared by reacting an appropriate erythro 2-bromo-1-[1,4-benzodioxan-2-yl]ethanol with 4-benzamidopiperidine, hydrolysing the product to remove the benzoyl group to give the erythro 4-aminopiperidine derivatives of formula IV; which compound may be alkylated to give 4-loweralkylamino derivatives.

The invention also includes pharmaceutical compositions containing as active ingredient an active compound of formula I as above defined. The active compound may be micronised if desired. In addition to the active ingredient, the compositions also contain a nontoxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substance which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formation of an active ingredient with encapsulating material as carrier to give a capsule in which the active ingredient (with or without other carriers) is surrounded by carrier, which is thus in association with it. Similarly cachets are included.

Sterile liquid form compositons include sterile solutions, suspensions, emulsions, syrups and elixirs. The active ingredient can be dissolved or suspended in a pharmaceutically acceptable sterile liquid carrier, such as sterile water, sterile organic solvent or a mixture or both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many orally either in liquid or solid composition form.

Preferably the pharmaceutical composition is in unit dosage form. In such form, the composition is subdivided in unit doses containing appropriate quantities of the active ingredients; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The following examples illustrates the invention; and the preparation of intermediates.

EXAMPLE 1

1-Benzoyl-3-[1-(2-[1,4-benzodioxan-2-yl)-2-oxoethyl]-piperid-4-yl]urea

1-Benzoyl-3-(piperid-4-yl)urea (2.46 g, 0.01 mol) and 2-bromoacetyl-1,4-benzodioxan (2.57 g, 0.01 mol) in dry dimethylformamide (40 mls) were stirred at room temperature. Triethylamine (1,1 g, 1.5 cm$^3$) was added and the suspension stirred for 1 hour. Water was added and the solid filtered off (4.20 g, 100%). The solid was suspended in methanol (40 mls) and ethanolic hydrogen chloride added until the solution was acidic. The title compound was filtered off as the hydrochloride salt and dried (yield 3.51 gm 76% yield). Melting pt. 160°-161° C.

Analysis $C_{23}H_{25}N_3C_2 \cdot HCl$ requires C, 60.06; H, 5.70; N, 9.14%. Found; C, 60.12; H, 5.71; N, 9.02%

EXAMPLE 2a

Threo 1-benzoyl-3-[1-(2-[1,4-benzodioxan-2-yl]-2-hydroxyethyl)piperid-4-yl]-urea 1-Benzoyl-3-[1-(2-[1,4-benzodioxan-2-yl]-2-oxoethyl)piperid-4-yl]-urea (7.21 g, 0.017 mol) was suspended in methanol (80 cm$^3$) and was stirred at room temperature. Sodium borohydride (1.0 g, 0.026 mol) in 2N sodium hydroxide (10 cm$^3$) was added dropwise to the stirring solution and then left to stir for a further hour. Water was added and the solid filtered off and dried (5.41 g, 75%). A. T.L.C. of a small portion of the solid was run in freshly prepared toluene: ethanol: 0.880 ammonia (90:10:1 by volume) on a silica plate and was found to contain two components having R$_F$ values of about 0.30 and 0.34. The solid was recrystallised from n-butyl acetate (9 times) to give the component (1.19 g) with the lower R$_F$ value. This was suspended in a small amount of methanol and ethanolic HCl added until the solution was just acidic. The hydrochloride of the title compound (0.96 g, 74%) was collected.

Melting pt. 212°-214° C.

Microanalysis $C_{23}H_{27}N_3O_5 \cdot HCl\frac{1}{4}H_2O$ requires C, 59.22 H, 6.15, N, 9.01%. Found: C, 59.22, H, 6.44, N, 8.50%.

EXAMPLE 2b

Erythro 1-benzoyl-3-[1-(2-[1,4-benzodioxan-2-yl]-2-hydroxyethyl)piperid-4-yl ]-urea, The method liquors from the first five recrystallisations obtained in Example 2b above were combined, evaporated and recrystallised from n-butyl acetate (4 times) to give the component with the higher R$_F$ value (0.34 approx) (0.9 g). This was suspended in a small amount of methanol and ethanolic hydrogen chloride added until the solution was just slightly acidic. The hydrochloride of the title compound (0.63 g, 64%) was collected.

Melting pt. 213°-216° C.

Microanalysis $C_{23}H_{27}N_2O_5 \cdot HCl$ requires C, 59.80; H, 6.11; N, 9.1%. Found: C, 59.46; H, 6.30; N, 8.9%.

EXAMPLE 3

(a) Erythro 1-(1,4-Benzodioxan-2-yl)-2-bromoethanol

2-Bromoacetyl-1,4-benzodioxan(53.8 g) in methanol (500 mls) was cooled to −70° C. Sodium borohydride (10.3 g) was added and the solution stirred at −70° C. for 12 hours. The solution was treated with hydrobromic acid until acidic and the solvent evaporated. The residue was dissolved in ether and the ether extracts were washed with sodium bicarbonate solution; then water and dried (MgSO$_4$) and evaporated to give a white solid. This was recrystallised eight times from petroleum spirit 60-80 to give 14 grams of the title compound.

(b) Erythro-4-benzamido-1-[2-(1,4-benzodioxan-2-yl)-2-hydroxyethyl]piperidine Erythro 1-(1,4-benzodioxan-2-yl)-2-bromoethanol (7.03 g 0.03 m). 4-benzamidopiperidine (5.59 g 0.027 m) and triethylamine (4 g 0.04 m) were refluxed in ethanol (250 mls) for 24 hours. The solvent was evaporated and the residue dissolved in chloroform and the chloroform extract washed with water, dried ($MgSO_4$) and evaporated to give a white solid (7.95 g 69%). This solid (1.5 g) was dissolved in the least amount of methanol and acidified with ethanolic HCl. The title compound crystallized, was filtered off and dried (1.04 g)

Melting pt. 246°–249° C.

Microanalysis; $C_{22}H_{26}N_2O_4 \cdot HCl$ requires C, 63.08%; H, 6.50%; N, 6.69%; Found: C, 62.99%; H, 6.55%; N, 6.39%

(c) Erythro 4-amino-1-[2-(1,4-benzodioxan-2-yl)-2-hydroxyethyl]-piperidine

Erythro-4-benzamido-1-[2-(1,4-benzodioxan-2-yl)-2-hydroxyethyl]piperidine (14.23 g) prepared according to Example 3(b) was suspended in 6 N hydrochloric acid (250 mls) and boiled under reflux for 8 hours. The solid was filtered off and washed with water. The aqueous filtrate and washings were treated with anhydrous potassium carbonate powder until basic and these extracted with chloroform. The combined chloroform extracts were washed with water, dried ($MgSO_4$), and evaporated to give title compound (10.4 g 100%)

EXAMPLE 4

Erythro 1-Cyclohexyl-3-[1-(2-[1,4-benzodioxan-2-yl]-2-hydroxyethyl)piperid-4-yl]urea, Erythro 4-amino-1-[2-(1,4-benzodioxan-2-yl)-2-hydroxyethyl]piperidine (2.0 g, 0.0072 m) prepared according to Example 3(c) in sodium dried benzene was treated with cyclohexyl isocyanate (0.99 g 0.008m) in sodium dried benzene (25 mls). The mixture was stirred at room temperature for 18 hours. The solid was filtered off and washed with benzene. The white solid was suspended in ethyl acetate and acidified with ethanolic hydrogen chloride until the solution was acidic. The title compound was filtered off, washed with ether and dried (1.47 g 46.5%)

Melting pt. 214°–216° C.

Microanalysis $C_{22}H_{33}N_3O_4 \cdot HCl$ requires C, 60.06%,; H, 7.79%; N, 9.55%. Found: C, 60.04%; H, 7.81% N, 9.58.

EXAMPLE 5

Erythro 1-phenyl-3-[-b 1-(2-[1,4-benzodioxan-2-yl]-2-hydroxyethyl)piperid-4-yl]urea Erythro 4-amino-1-[2-(1,4-benzodioxan-2-yl)-2-hydroxyethyl]piperidine (2.0 g 0.007 m) prepared according to Example 3(c) was dissolved in sodium dried benzene (100 mls). To the stirring solution was added phenyl isocyanate (0.76. 0.0072 m) in sodium dried benzene (25 mls). The solution was stirred at room temperature for 18 hours. The solid was filtered off, then dissolved in ethanol and acidified with ethanolic hydrogen chloride to give the hydrochloride salt of the title compound, (0.87 g 28%).

Melting pt: 214°–215° C.

Microanalysis: $C_{22}H_{27}N_3O_4 \cdot HCl$ requires C,60.89%; H, 6.50%; N, 9.68%. Found: C, 60.88; H, 6.45%; N, 9.82%.

EXAMPLE 6

Erythro 1-p-methoxybenzoyl-3-[1-(2-[1,4-benzodioxan-2-yl]-2-hydroxyethyl)piperid-4-yl]urea Erythro 4-amino-1-[2-(1,4-benzodioxan-2-yl)-2-hydroxy-ethyl]piperidine (2.0 g 0.0072 m)) was dissolved in sodium dried benzene (100 mls). To the stirring solution was added p-methoxy benzoyl isocyanate (1.27 g 0.0072m) in benzene (20 mls) and the solution stirred at room temperature for 18 hours. The solvent was evaporated and the residue heated with isopropyl alcohol. The insoluble solid was filtered off and triturated with hot ethanol, filtered and dried to give the title compound (0.5 g 15%).

Melting pt: 198°–199° C.

Microanalysis: $C_{24}H_{29}N_3O_6 \cdot \frac{1}{2}H_2O$ requires C, 62.06% H, 6.51%; N,9.05%. Found C, 62.08%; H, 6.39%; N, 9.01%.

EXAMPLE 7

Erythro 1-p-chlorobenzoyl-3-[1-(2-[1,4-benzodioxan-2-yl]-2-hydroxyethyl)piperid-4-yl]thiourea Ammonium thiocyanate (0.6 g 0.0076 m) was stirred in dry acetone (7 mls) and p-chlorobenzoyl chloride (1.26 g 0.0072 m) was added and the solution refluxed for 5 minutes. Erythro 4-amino-1-[-b 2-(1,4-benzodioxan-2-yl)-2-hydroxyethyl]piperidine (2.0 g 0.0072 m) in dry acetone (15 ml) was added to the hot solution and the mixture refluxed for 15 minutes. The solution was poured into water and the resulting precipitate was extracted with chloroform, dried ($MgSO_4$), and evaporated to give a solid which was recrystallised from ethanol. The recrystallised material was dissolved in ethanol and acidified with ethanolic hydrogen chloride to give the hydrochloride salt of the title compound (0.65 g 20%).

Melting Pt: 187°–189° C.

Microanalysis: $C_{23}H_{26}N_3ClO_4SHCl \cdot \frac{1}{2}H_2O$ requires C, 52.77%; H, 5.39%; N, 8.03%. found: C, 52.77%; H, 5.39%; N,8.03%.

EXAMPLE 8

Repeating the procedure of Example 4(when X is oxygen) or Example 7(when X is sulphur) the following compounds of formula I may be prepared according to the reaction:

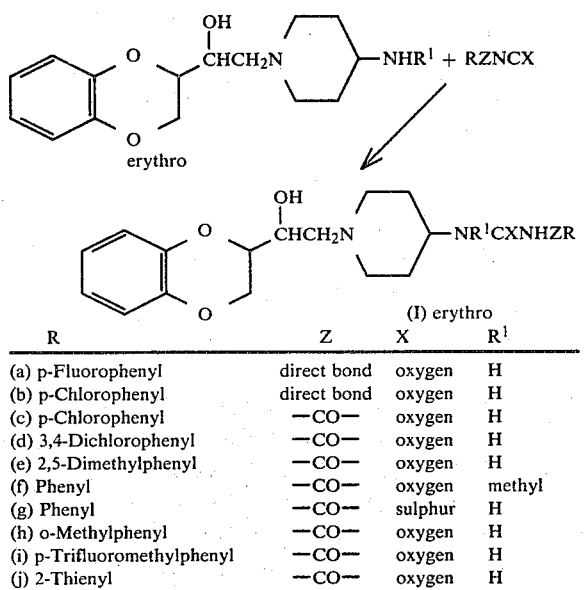

| R | Z | X | R¹ |
|---|---|---|---|
| (a) p-Fluorophenyl | direct bond | oxygen | H |
| (b) p-Chlorophenyl | direct bond | oxygen | H |
| (c) p-Chlorophenyl | —CO— | oxygen | H |
| (d) 3,4-Dichlorophenyl | —CO— | oxygen | H |
| (e) 2,5-Dimethylphenyl | —CO— | oxygen | H |
| (f) Phenyl | —CO— | oxygen | methyl |
| (g) Phenyl | —CO— | sulphur | H |
| (h) o-Methylphenyl | —CO— | oxygen | H |
| (i) p-Trifluoromethylphenyl | —CO— | oxygen | H |
| (j) 2-Thienyl | —CO— | oxygen | H |

EXAMPLE 9

1-Cyclohexylcarbonyl-3-[1-(2-[1,4-benzodioxan-2-yl]-2-hydroxyethyl)piperid-4-yl]urea 1-Cyclohexylcarbonyl-3-[1-(2-[1,4-benzodioxan-2-yl]-2-oxoethyl)piperid-4-yl]urea, prepared by reacting 1-cyclohexylcarbonyl-3-(piperid-4-yl)urea with 2-bromoacetyl-1,4-benzodioxan in DMF/Et₃N, may be reduced using sodium borohydride in 2 N sodium hydroxide to give the title compound.

EXAMPLE 10

1-[2-Thienyl]-3-[1-(2-[1,4-benzodioxan-2-yl]-2-hydroxyethyl)piperid-4-yl]urea

1-[2-Thienyl]-3-[1-(2-[1,4-benzodioxan-2-yl]-2-oxoethyl)piperid-4-yl]urea, prepared by reacting 1-(piperid-4-yl)-3-(2-thienyl)urea with 2-bromoacetyl-1,4-benzodioxan in DMF/Et₃N, may be reduced using sodium borohydride in 2 N sodium hydroxide to give the title compound.

EXAMPLE 11

1-[1-(2-[1,4-benzodioxan-2-yl]-2-hydroxyethyl)piperid-4-yl]urea

The title compound may be prepared by hydrolysis of 1-benzoyl-3-[1-(2-[1,4-benzodioxan-2-yl]-2-hydroxyethyl)-piperid-4-yl]urea using aqueous sodium hydroxide.

EXAMPLE 12

1-[2-Furoyl]-3-[1-(2-[1,4-benzodioxan-2-yl]-2-hydroxyethyl)piperid-4-yl]urea

1-[2-Furoyl]-3-[1-(2-[1,4-benzodioxan-2-yl]-2-oxoethyl)piperid-4-yl]urea, prepared by reacting 1-(piperid-4-yl)-3-(2-Furoyl)urea with 2-bromoacetyl-1,4-benzodioxan in DMF/Et₃N, may be reduced using sodium borohydride in 2 N sodium hydroxide to give the title compound.

EXAMPLE 13

Erythro 1-benzoyl-3-[1-(2-[6-methoxy-1,4-benzodioxan-2-yl]-2-hydroxyethyl)piperid-4-yl]urea Using the procedure of Example 4 erythro 4-amino-1-[2-(6-methoxy-1,4-benzodioxan-2-yl)-2-hydroxyethyl]-piperidine may be reacted with benzoyl isocyanate to give the title compound.

EXAMPLE 14

Erythro 1-benzoyl-3-[1-(2-[1,4-benzodioxan-2-yl]2-hydroxyethyl)piperid-4-yl]urea Erythro 1-(1,4-benzodioxan-2-yl)-2-bromoethanol (7.04 g), 3-benzamido-1-(piperid-4-yl)urea (6.65 g) and triethylamine (4 g) were refluxed in ethanol (250. cm³) for 24 hours. The solvent was evaporated and the residue dissolved in chloroform. The chloroform extract was washed with water, dried (MgSO₄) and evaporated to give a white solid. This was suspended in ethanol (200 cm³) and acidified with ethanolic hydrogen chloride. The title compound (hydrochloride salt) crystallised out and was filtered off and dried. (8.85 g (71%).
Melting point. 206°–207° C.
$C_{23}H_{27}N_3O_5$. HCl requires C, 59.80%; H, 6.11%; N, 9.10%. Found: C, 59.58%; H, 5.95; N, 9.04%.

We claim:

1. A method of treating or preventing coronary artery disorders in a warm blooded animal afflicted with a disorder requiring β-blocking therapy, which comprises administering to said animal a therapeutically effective amount therefor of a compound having the formula

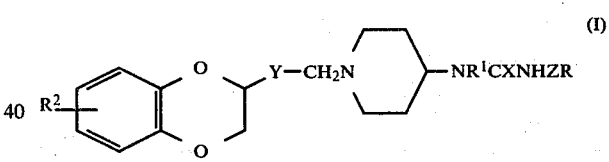

in which:
X represents oxygen or sulphur;
Y represents —CHOH—;
Z represents

or a direct bond;
R represents cycloaklyl group having 5 to 7 carbon atoms; phenyl; phenyl substituted by at least one member selected from the group consisting of halogen, lower alkyl, lower alkoxy, methylenedioxy, perhalo lower alkyl, nitro, amino and hydroxy; thienyl, furyl or pyridyl; or when Z is a direct bond R also represents hydrogen;
R¹ represents hydrogen or lower alkyl;
and
R² represents hydrogen, halogen, lower alkyl or lower alkoxy;
or
a pharmaceutically acceptable acid addition or quaternary ammonium salt thereof, together with a pharmaceutically acceptable carrier.

* * * * *